United States Patent
Samadani et al.

(10) Patent No.: US 12,249,427 B2
(45) Date of Patent: Mar. 11, 2025

(54) PREDICTION OF VENTILATOR-ASSOCIATED PNEUMONIA (VAP)

(71) Applicant: KONINKLIJKE PHILIPS N.V., Eindhoven (NL)

(72) Inventors: Ali Akbar Ahmad Samadani, Cambridge, MA (US); Taiyao Wang, Cambridge, MA (US); Cornelis van Zon, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 263 days.

(21) Appl. No.: 17/879,240

(22) Filed: Aug. 2, 2022

(65) Prior Publication Data
US 2023/0110196 A1   Apr. 13, 2023

Related U.S. Application Data (60) Provisional application No. 63/254,283, filed on Oct. 11, 2021.

(51) Int. Cl.
*G16H 50/30* (2018.01)
(52) U.S. Cl.
CPC .................................. *G16H 50/30* (2018.01)
(58) Field of Classification Search
CPC ........ G16H 50/30; G16H 20/40; G16H 50/20; G16H 50/70; G16H 40/67
USPC ......................................................... 705/2–3
See application file for complete search history.

(56) References Cited

U.S. PATENT DOCUMENTS

| | | | |
|---|---|---|---|
| 2011/0029248 A1* | 2/2011 | Saeed | A61M 16/0051 702/19 |
| 2014/0230819 A1* | 8/2014 | Rawlins | A61M 16/021 128/204.23 |

OTHER PUBLICATIONS

Giang et al., "Predicting ventilator-associated pneumonia with machine learning." Medicine, 2021, 100(23), p. 26246 (Year: 2021).*
"How-to Guide: Prevent Ventilator-Associated Pneumonia." Cambridge, MA: Institute for Healthcare Improvement; 2012 (Year: 2012).*
5 Million Lives Campaign. "Getting Started Kit: Prevent Ventilator-Associated Pneumonia: How-to Guide." Cambridge, MA: Institute for Healthcare Improvement; 2012.
Papazian, L. et al., "Ventilator-associated pneumonia in adults: a narrative review." Intensive care medicine, (2020) 46(5), 888-906.

(Continued)

*Primary Examiner* — Joy Chng
(74) *Attorney, Agent, or Firm* — Daniel H. Brean; Andrew M. Gabriel (57) ABSTRACT

Described herein are methods, devices and systems for predicting ventilator associated pneumonia (VAP). In an example, data of a patient including one or more features useful in predicting VAPs are accessed and the features are extracted. A model is activated based on a time parameter associated with mechanical ventilation or length of stay in ICU. The extracted features are evaluated automatically by the activated model to determine a probability that a VAP will occur. If it is determined, based on the evaluating, that a VAP has a probability of occurring that exceeds a threshold, an indication that the VAP is predicted to occur may be provided. Other examples are disclosed and claimed.

16 Claims, 8 Drawing Sheets

(56) References Cited

OTHER PUBLICATIONS

Zimlichman, E. et al., "Health care-associated infections: a meta-analysis of costs and financial impact on the US health care system." JAMA internal medicine, (2013)173(22), 2039-2046.

Giang, C. et al., "Predicting ventilator-associated pneumonia with machine learning." Medicine, (2021) 100(23), p. e26246.

Kalil, A.C. et al., "Management of adults with hospital-acquired and ventilator-associated pneumonia: 2016 clinical practice guidelines by the Infectious Diseases Society of America and the American Thoracic Society." (2016) Clinical Infectious Diseases, 63(5), e61-e111.

NHSN. Pneumonia (Ventilator-associated [VAP] and nonventilator-associated Pneumonia [PNEU]) Event. 2021. http://www.cdc.gov/nhsn/pdfs/pscmanual/6pscvapcurrent.pdf.

Centers for Disease Control and Prevention. Ventilator-associated event (VAE), Jan. 2019. URL: https://www.cdc.gov/nhsn/PDFs/pscManual/10-VAE_FINAL.pdf.

He, Q. et al., "The epidemiology and clinical outcomes of ventilator-associated events among 20,769 mechanically ventilated patients at intensive care units: an observational study." Critical Care, (2021)25(1), 1-11.

Wu, V.K.S et al., "Prevalence, clinical characteristics, and outcomes related to ventilator-associated events in neurocritically Ill patients." Neurocritical Care (2020) 33(2), 499-507.

Fabre, V. et al., "Does this patient need blood cultures? A scoping review of indications for blood cultures in adult nonneutropenic inpatients." Clinical Infectious Diseases, (2020) 71(5), 1339-1347.

\* cited by examiner

PREDICTION OF VENTILATOR-ASSOCIATED PNEUMONIA (VAP)

CROSS-REFERENCE TO RELATED APPLICATIONS

This patent application claims the priority benefit under 35 U.S.C. § 119(e) of U.S. Provisional Application No. 63/254,283, filed on Oct. 11, 2021, the contents of which are herein incorporated by reference.

FIELD OF THE INVENTION

The subject matter described herein generally relates to a clinical decision support system (CDS) and related tools offering automated techniques for using medical data to predict ventilator-associated pneumonia (VAP).

BACKGROUND OF THE INVENTION

Patients receiving mechanical ventilation (MV) are at high risk of developing complications including ventilator-associated pneumonia (VAP). VAP is an infection that starts at least 48 hours into a mechanical ventilation episode with many negative outcomes including increased mortality, morbidity, and prolonged length of stay (LOS). VAP accounts for 32% of hospital acquired infections, affecting up to 40% of patients mechanically ventilated for greater than two days. Furthermore, VAP imposes a significant financial burden on healthcare systems, in some cases adding $40,000 in cost per hospital stay.

Despite the significance of VAP in patient and hospital outcomes, accurate, early detection and treatment of VAP remains a major predicament.

SUMMARY OF THE INVENTION

Various embodiments provide methods, devices, products and systems for predicting ventilator-associated pneumonia (VAP). In an embodiment, medical data of a patient, including a time parameter such as a mechanical ventilation (MV) time or a length of stay (LOS) in an intensive care unit (ICU), and one or more features useful in predicting VAP are accessed and used to activate a prediction model to evaluate the one or more features and to determine a probability that a VAP will occur. If it is determined, based on the evaluating, that a VAP has a probability of occurring that exceeds a threshold, an indication that the VAP is predicted to occur may be provided.

In summary, an embodiment provides a method of predicting ventilator associated pneumonia (VAP), comprising: accessing (410a), using a processor, data of a patient comprising one or more features; determining (420a), using a processor, a time parameter associated with mechanical ventilation of the patient; using (430a) the time parameter to activate one of an early VAP model and a late VAP model to provide an activated model; and providing (460a), using a processor, a prediction that VAP will occur based on the activated model operating on the one or more features of the patient data.

Another embodiment provides a system for predicting ventilator associated events, comprising: an output device (111); a processor (510) operatively coupled to the output device; and a memory (550) operatively coupled to the processor, the memory comprising processor-executable code comprising: code that accesses (103) data of a patient comprising one or more features; code that determines (105) a time parameter associated with mechanical ventilation of the patient; code that uses (105) the time parameter to activate one of an early VAP model and a late VAP model to provide an activated model; and code that provides (107) a prediction that VAP will occur based on the activated model operating on the one or more features of the patient data.

A further embodiment provides a ventilator (102), comprising: a non-transitory storage medium (550) having processor-executable code comprising: code that accesses (103) data of a patient comprising one or more features; code that determines (105) a time parameter associated with mechanical ventilation of the patient; code that uses (105) the time parameter to activate one of an early VAP model and a late VAP model to provide an activated model; and code that provides (107) a prediction that VAP will occur based on the activated model operating on the one or more features of the patient data.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION OF EMBODIMENTS

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the claims, but is merely representative of those embodiments.

Reference throughout this specification to "embodiment(s)" (or the like) means that a particular feature, structure, or characteristic described in connection with the embodiment is included in at least one embodiment. Thus, appearances of the phrases "according to embodiments" or "an embodiment" (or the like) in various places throughout this specification are not necessarily all referring to the same embodiment.

As used herein, the singular form of "a", "an", and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware. The term "about" or "approximately" as used herein includes conventional rounding of the last significant digit.

Furthermore, the described features, structures, or characteristics may be combined in any suitable manner in one or more embodiments. In the following description, numerous specific details are provided to give a thorough understanding of example embodiments. One skilled in the relevant art will recognize, however, that aspects can be practiced without one or more of the specific details, or with other methods, components, materials, etc. In other instances, well-known structures, materials, or operations are not shown or described in detail to avoid obfuscation.

Accurate and early prediction of ventilator associated pneumonia (VAP) remains challenging. This is in part due to the lack of a standard and reliable clinical definition of VAP, the absence of which often leads to inaccurate, missing or delayed VAP detection and precludes its prediction. Therefore, there is a need for a clinical decision support system (CDS) that can identify patients at high risk of VAP in advance and help enable early interventions. In addition to the one-time risk estimation, it may be desirable for CDS tools to allow for a serial or ongoing evaluation of patients, e.g., to account for recent changes in patient status that might be linked to a different risk of developing VAP.

In an embodiment, data is curated to provide an adequate basis for models that predict early and late VAP. In one example, data is curated using a set of criteria for labeling VAP events in clinical datasets, including onset time. This may be accomplished, by way of example, through consolidating clinical guidelines from various sources such as the Infectious Disease Society of America/American Thoracic Society (IDSA/ATS), and the US Centers for Disease Control and Prevention (CDC). Labeled datasets including onset time for events of interest are prepared for different modalities such as vitals, lab or culture results, ventilator settings, etc., for both positive and negative VAP samples. In one example, the labeled datasets include a label of positive or negative VAP, positive or negative early VAP, or positive or negative late VAP. The different labels for early-onset VAP and late-onset VAP permit an embodiment to leverage positive and negative samples, for both early and late VAP, to form models for predicting each.

An embodiment employs a hybrid approach for predicting VAP. In one example, an early VAP model is trained using the labeled datasets related to early VAP, i.e., utilizing an onset time and associated features of interest for early-onset VAP in the labeled dataset. Likewise, a late VAP model is trained using the labeled datasets associated with late-onset VAP.

In an embodiment, a patient's length of stay (LOS) at the time of prediction is used in a VAP risk probability determination, i.e., it is explicitly accounted for in the VAP prediction evaluation. This permits an embodiment to distinguish early-onset VAP events from late-onset VAP events, which might manifest differently due to factors such as multidrug resistant (MDR) infections prevalent late in the course of hospitalization. By way of example, two models or two sub-models, one for each of early-onset VAP and late-onset VAP, are utilized. In an embodiment a specific model or sub-model is activated for VAP prediction(s) made before a time threshold delineating early-onset and late-onset VAP, whereas another specific model or sub-model is activated for VAP prediction(s) made after the threshold. In an embodiment, the process is coordinated or aware of temporal correctness. For example, in an embodiment, the early and late VAP models may be coordinated, e.g., using an output from an early VAP model, such as its last prediction, as a feature for a late VAP model's first prediction.

The description now turns to the figures. The illustrated example embodiments will be best understood by reference to the figures. The following description is intended only by way of example and simply illustrates certain selected example embodiments representative of the invention, as claimed.

Figure 1:
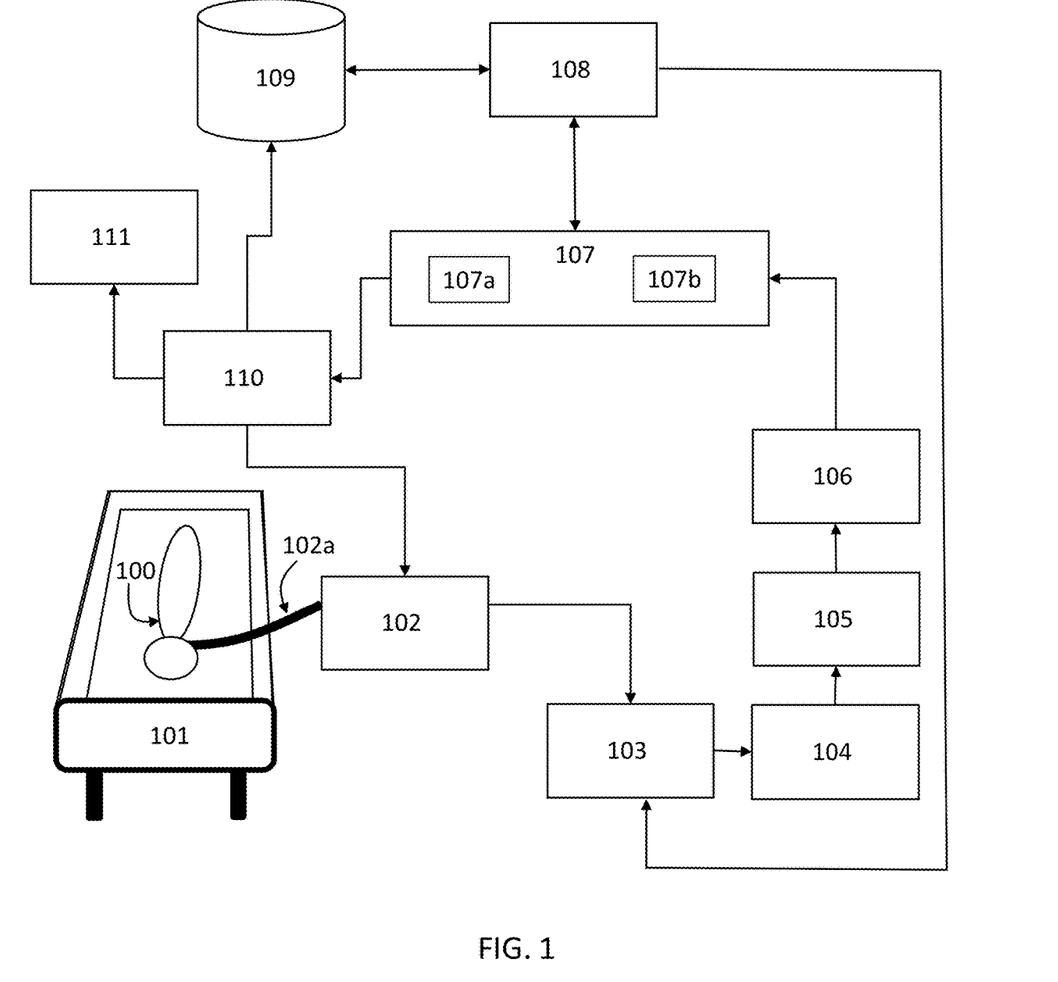
FIG. 1 illustrates an example system for automatically predicting VAP.

Referring to FIG. 1, an example system is illustrated for automatically predicting VAPs. In the example of FIG. 1 a system includes a ventilator 102 that provides invasive mechanical ventilation via an oxygen delivery system 102a, e.g., including a breathing tube, to a patient 100. The ventilator 102 is a source for data useful in making VAP predictions and is therefore communicatively coupled to a data acquisition module 103, e.g., where a module may be a module of executable code configured to operate with a processor as described herein. For example, the ventilator 102 may provide data related to ventilator settings, such as positive end-expiratory pressure (PEEP) and fraction of inspired oxygen ($F_iO_2$), time of ventilation, length of stay (LOS) in ICU, etc., which may be used by an automated prediction system as further described herein.

The data acquisition module 103 communicates with the ventilator 102 and electronic medical record (EMR) or electronic health record (EHR) system 108 to retrieve patient medical data such as recent and long-term patient chart data for a patient 100. For example, the data acquisition module 103 may retrieve or access ventilator settings data, ventilation type and mode, lab or culture results, antibiotic treatments, and a patient's physiological data, along with a patient's demographics, comorbidities, diagnoses and the like. As with other modules, the data acquisition module 103 may use standard protocols and APIs, e.g., Fast Healthcare Interoperability Resources (FHIR), to communicate and extract data from EMR or EHR system 108, a bedside physiological monitor 111, ventilator 102, etc.

The data acquisition module 103 may be configured to receive data periodically, continuously or may dynamically adjust its data acquisition. In an embodiment, the system uses the data by segmenting it, processing it, and extracting features from the resulting segments for evaluation according to a machine learning or artificial intelligence model, e.g., a trained classifier as described herein. In an embodiment, certain data may be used to adjust or change the model, e.g., a time parameter associated with MV time, as different VAP models or sub-models may be used to predict VAP depending on the time of ventilation for the patient 100 in association with the time of VAP prediction.

Figure 2A:
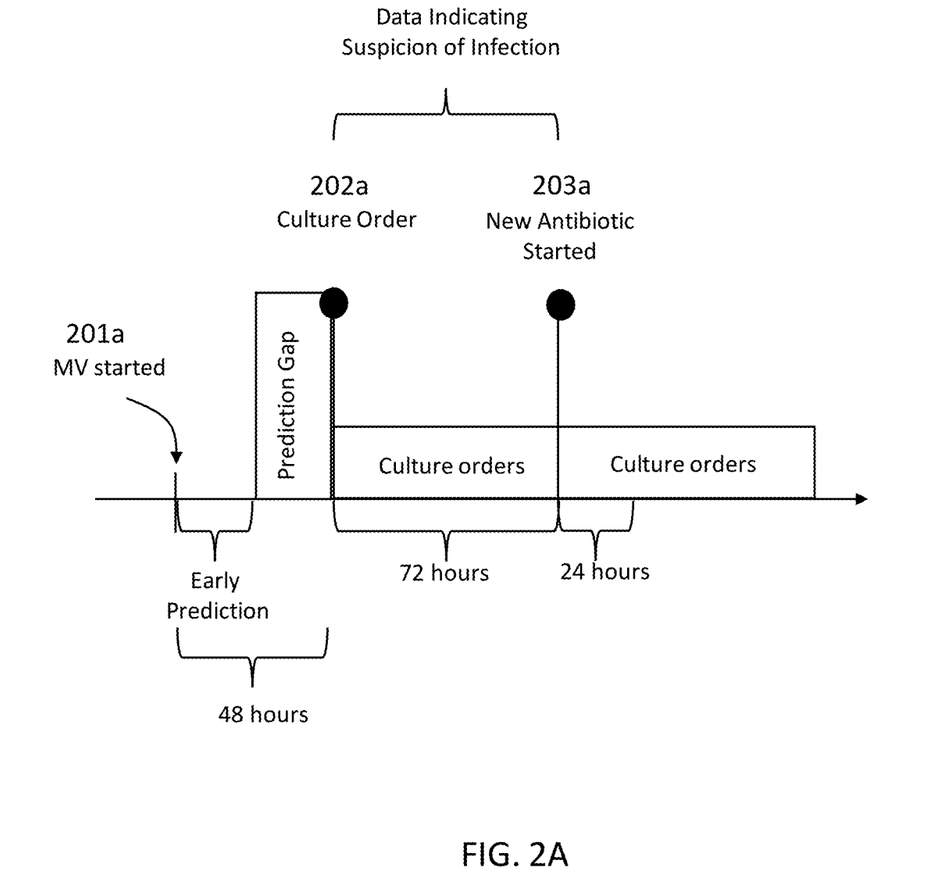
FIG. 2A illustrates an example of marking criteria used to prepare labeled training data for a VAP detection module.

Referring to FIG. 2A, an example of VAP criteria (a set of rules created considering one or more clinical guidelines) are used to tag and extract VAP events from EMR data. This provides data for forming model(s) of an embodiment that can be used to calculate and monitor the probability of VAP and to provide an early prediction as to when VAP is predicted to occur. In the example of FIG. 2A, training datasets associated with MV time in the ICU may be formed using the VAP criteria indicated. The absence of ground truth data for VAP events and their timing poses a significant challenge to the development of predictive models. In the medical literature, while there are some necessary and general criteria for VAP identification, there is no conventional clinical definition that provides sufficient, sensitive, and specific criteria for automated VAP detection or prediction.

Previous works on computational models for management of VAPs rely on International Classification of Disease (ICD) codes for identifying patients with VAP events. This approach has several problems that obstruct and invalidate any VAP prediction claim made by such models. For example, this approach does not provide the exact VAP onset time; therefore, no prediction can be claimed. Further, even if limited to a one-shot prediction at a preset time (e.g., 48 hours after intubation), the prediction time might overlap with the VAP window (temporal window where VAP is present and has already been clinically observed) as high as in 20% of cases in the Medical Information Mart for Intensive Care (MIMIC III) EMR dataset. Finally, ICD codes are not a reliable indicator of adverse events, including VAP, during patient stays because they are designed and used for billing purposes. In this respect, it is worth noting the insufficiency of ICD codes or related codes given that complications such as VAP are under-reported in ICD codes, e.g., only 3% of mechanically-ventilated patients in the MIMIC III clinical dataset have VAP-related ICD codes, while the incidence rate of VAP is known to be as high as 40% of mechanically-ventilated patients in the clinical literature.

As illustrated in FIG. 2A, a step in building data-driven predictive models used by an embodiment is to curate a dataset of MV episodes with ground truth for VAP and non-VAP events, including accurately marking VAP onset in historical medical data utilized for training or forming the models. An embodiment uses a set of criteria stemming from clinical guidelines to detect and mark, after the start of MV 201a, the time of clinical suspicion of infection 202a and then create ground truth for VAP events and their onset time from within the suspected infection event set. In an embodiment, the VAP labelling criteria also makes use of MV start time 201a, time of administration of new antimicrobial agents 203a, and timing of any microbiological tests (culture ordering), as described herein.

VAP events are heterogenous in their clinical and pathologic manifestations. Such intra-VAP variabilities obscure features most salient to distinguishing VAP events from non-VAP events. One such variability results from the VAP onset time relative to the ICU admission time. An embodiment provides a framework to separate early VAPs from late VAPs and builds predictive model(s) that explicitly incorporate VAP onset time from training data in making predictions using these models.

The extracted VAP events can be used to curate the appropriate datasets for training of early and late VAP prediction models. In the particular example shown in FIG. 2A, EMR system data indicating clinical suspicion of infection such as culture order 202a or new antibiotic treatment 203a are marked. In a specific example, any indication of ordered culture 202a or new antibiotic treatment 203a are marked as clinical suspicions of infection and time-stamped labels of each are used with respect to the start of MV 201a to denote a time of suspicion of clinical infection, such as evidenced by the earlier of 1) ordering of a microbial culture 202a, and 2) the start of a new antibiotic treatment 203a.

By way of specific, non-limiting example, as shown in FIG. 2A, within a temporal window beginning 48 hours after the start of MV 201a, and less than or equal to 72 hours after the extubation event, an embodiment searches EMR system data for antimicrobial agents used for treatment of lung and respiratory complications, e.g., such as determined from a list provided in the CDC Ventilator Associated Events (VAE) guideline. An embodiment detects anti-microbial agents that are new within the context, i.e., the administration of the agent has started after 48 hours into MV and was not administered in the preceding two days.

An embodiment searches EMR system data for microbiological test orders (culture orders) within the temporal window 72 hours prior to, and 24 hours after, the detected new antimicrobial agent, as indicated in FIG. 2A. An embodiment limits the culture types sought in the EMR system data to those obtained from the respiratory tract (e.g., sputum, endotracheal aspirate, bronchoalveolar lavage, lung tissue, or protected specimen brush) and/or blood cultures. An embodiment marks the onset of a clinical suspicion of infection as the earlier of the new antibiotic start time 203a agent and ordered culture time 202a, noting that the time ordering of these events may be reversed from the single example illustrated in FIG. 2A.

In one example, an embodiment marks VAP events in EMR system data from within the suspected infections identified per the example of FIG. 2A as those satisfying the following criteria: positive culture results, no indication of pneumonia in admission diagnosis, no indication of community-acquired pneumonia (CAP) in the discharge ICD codes, and the onset of clinical suspicion is equal to or greater than 48 hours after the start of MV 201a. These example criteria enable validation of down-stream VAP prediction models, as it can be ensured that prediction takes place accurately prior to any clinical suspicion of infection. Furthermore, by explicitly distinguishing between community acquired pneumonia (CAP) and VAP events in the VAP criteria used, an embodiment provides the opportunity to characterize each infection separately, learn about their respective salient features (e.g., responsible organisms), enables differential treatment, and enables reliable reporting of pneumonia cause, which impacts reimbursement.

In this regard, an embodiment characterizes a detected VAP event by its underlying pathogen or organisms and evaluates the later prediction performance for each organism family. This enables further refinement of VAP events, as filters may be applied to remove events with underlying organisms that are not typically associated with VAP. An embodiment qualifies the identified VAP events as early or late VAPs based on how far from ICU admission time or MV time they occur, e.g., following a guideline such as IDSA/ATS guideline that indicates early VAPs are VAP events beginning up to day four of ICU admission, and late VAPs are VAP events beginning on or after day four of ICU admission.

Referring back to FIG. 1, one or more prediction associated modules, e.g., components 104-107 of FIG. 1, communicate with a ventilator 102 and EMR system 108 to retrieve data related to VAP prediction. The retrieved data may be utilized to train one or more of the models, tune them during ongoing use, and to make VAP predictions during MV.

Figure 2B:
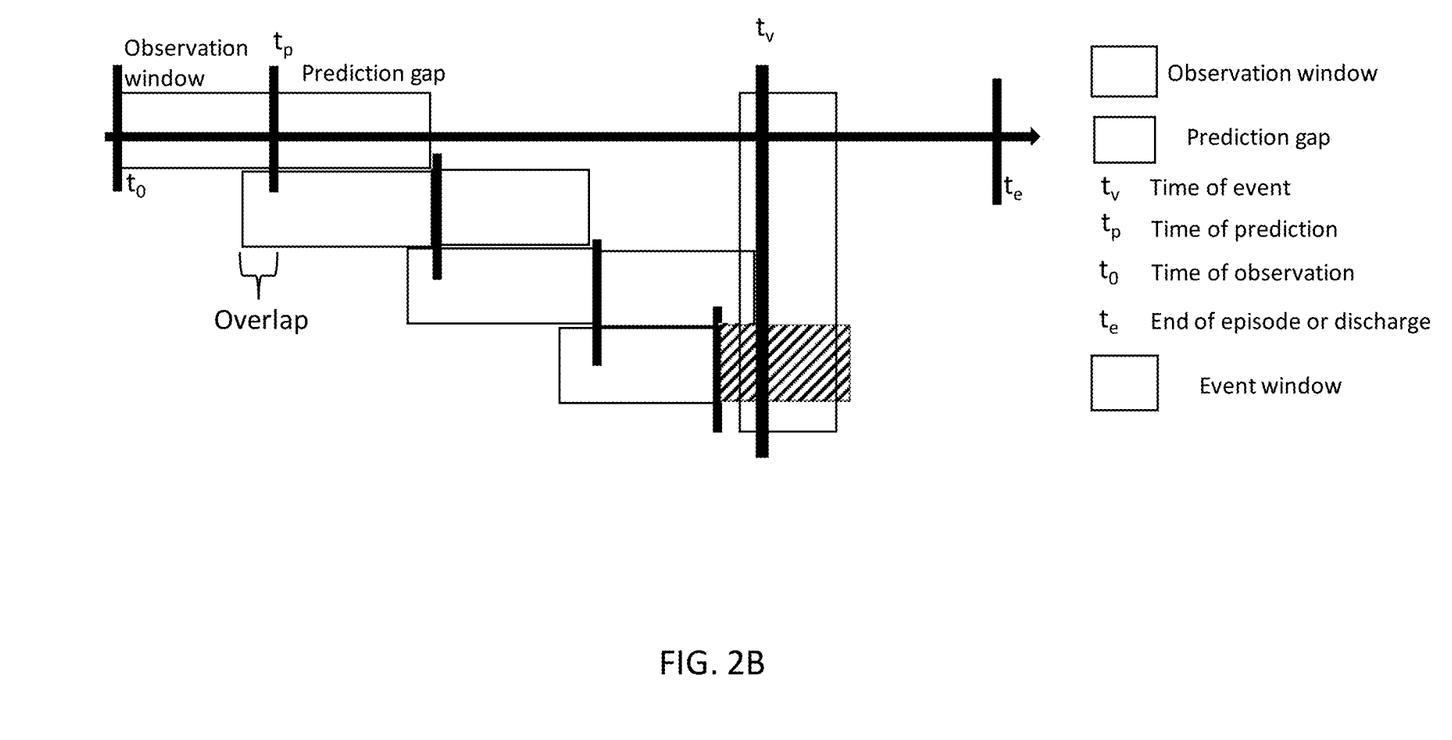
FIG. 2B illustrates an example of data segmentation.

Referring to FIG. 1 and FIG. 2B, in a model training and development phase, a data segmentation module 104 segments patient medical data for creation of a feature-based representation of patient data using four parameters 1) observation window, 2) prediction gap, 3) event window and 4) the amount of overlap (overlap). For episodes with no VAP event, the segmentation module 104 randomly samples a time point in each episode. Empirically, this results in a day-match negative (non-VAP) class, i.e., the distribution of randomly sampled time points in the non-VAP class matches that of the VAP class.

Next, the data segmentation module 104 segments the patient's data streams into windows (observation windows as illustrated in FIG. 2B) representing subsequent observations, with or without overlap between successive observation windows. Each observation window constitutes an observation sample based on which an occurrence of VAP is predicted in advance. How far in advance a VAP can be reliably predicted is referred to as the prediction gap, indicated by illustration in FIG. 2A and FIG. 2B. A temporal offset around a VAP event may be constructed as a window (event window), bounding the time around the impending event time ($t_v$). Thus, at observation time ($t_0$), an observation window (from $t_0$ to $t_p$) is used to predict if a VAP is likely to occur after the prediction gap. For each time a prediction is made ($t_p$), it is evaluated whether VAP is likely at a given time ($t_p$+prediction gap). This process may continue until the end of the MV episode or discharge ($t_e$).

A data processing module 105 may be used to receive the data from the data segmentation module 104 and processes the data through a cascade of filters and signal conditioning units to remove measurement and environmental disturbances and noise from the data. As with other elements, steps or processes, in an embodiment the ordering or arrangement of the elements, steps or processes may be changed. Different data streams may be processed using a different set of filter banks.

A feature extraction module 106 represents the segmented samples in terms of descriptive statistics of various physiological, clinical and lab measurements along with static features such as the patient's demographics and admission diagnosis. Furthermore, the module computes derived features inspired by ventilator associated event (VAE) definitions, i.e., any presence and the count of prior stable periods, where a stable period is a period of two consecutive days with stable or decreasing PEEP or $F_iO_2$ during MV, and any presence and the count of oxygen worsening (OW) events, where an OW event is when, over a period of 48 hours, there is an increase in PEEP or $F_iO_2$ of at least 3 points and 20%, respectively.

A prediction module 107 receives the extracted features representing data samples and determines whether a VAP event is likely to occur within a temporal horizon defined by the prediction gap (see FIG. 2B) using the prediction model(s). The output of the prediction module 107 can be interpreted as a VAP risk score. A risk score may be reported as an indication on an ongoing basis. A risk score exceeding a predetermined threshold may produce a specific type of indication, e.g., an alarm or an alert. The VAP risk score may be provided in a variety of ways, e.g., as a probability of a VAP occurring, trend line of such probabilities, etc.

In an embodiment, prior to deployment, the prediction module 107 may be trained and its performance verified using validation procedures, e.g., implemented using a model training and validation module 107a. For example, training and validation procedures may be implemented as a routine that can be repeated periodically or intermittently to ensure the model is in alignment with changes in data reporting models, baselines, care protocols, and guidelines over time. A training and validation routine may include a data set split into train, validation, and test sets and using the train set to train a predictive model. The validation set is used to tune model hyperparameters and the test set is a holdout set, previously unseen by the model, and is used to test the trained model. This process may be repeated a number of times to confirm the stability and performance of the model. The model verification process is often referred to as cross-validation.

In an embodiment, a VAP prediction model implemented using the prediction module 107 may be from any class of machine learning models such as but not limited to: logistic regression, decision trees, or deep learning models. Further, a VAP predictive model directly encoding temporal progression of time-series data (e.g., vital signs, ventilator settings, etc.) such as hidden Markov models or recurrent neural networks and their variations may be used. In the latter, model parameters or resulting time-series abstractions may be combined with other static features such as comorbidities and patient demographics to make the final prediction.

In an embodiment, the prediction module 107 includes a hyperparameter tuning module 107b. The parameters described herein in connection with the data segmentation module 104 (e.g., observation window duration, the amount of overlap (overlap), prediction gap duration, and event window duration) represent a set of hyperparameters of a prediction system. Other hyperparameters may include those specific to a class of machine learning models used e.g., number of decision trees. An optimal setting of these hyperparameters is used for improving prediction model performance and reliably predicting a VAP event. These hyperparameters may be tuned through an outer validation process (outer to the cross-validation for evaluation of model performance) using an optimization routine such as evolutionary algorithms, including particle swarm, as further described herein.

Figure 2C:
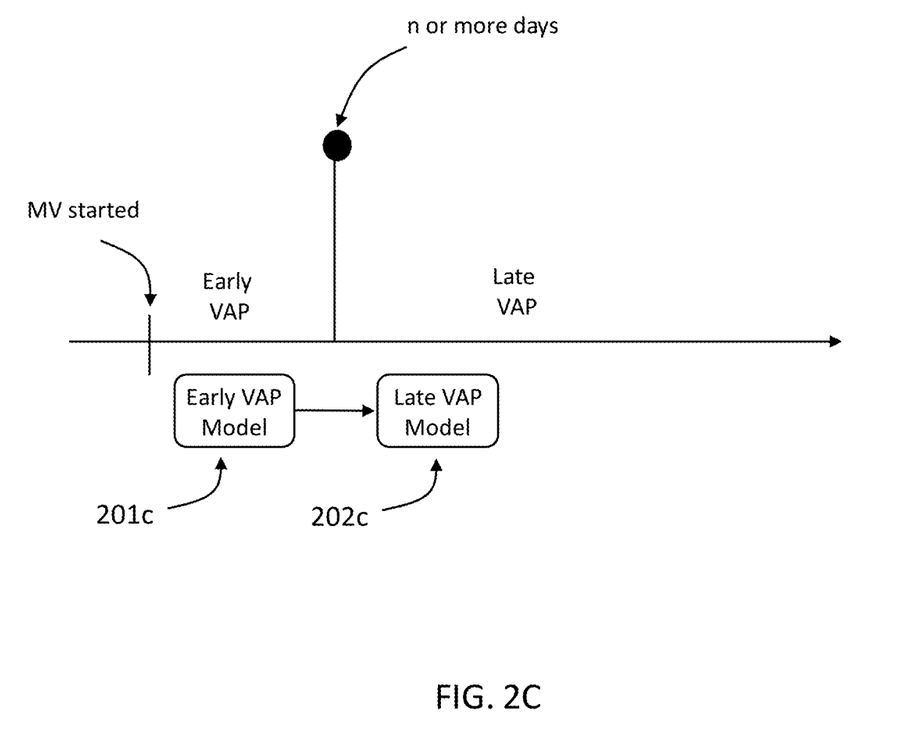
FIG. 2C illustrates an example hybrid model for early and late VAP detection.

As shown in FIG. 2C, an embodiment may train more than one model, e.g., an early VAP model 201c and a late VAP model 202c, for predicting early-onset VAP and late-onset VAP, respectively. In an embodiment, the early VAP model 201c and late VAP model 202c are trained using differential training sets, e.g., to tune the models 201c, 202c to predict early-onset VAP and late-onset VAP using different salient features in the different training sets. As described herein, these different training sets may be prepared using timing considerations as outlined in the example of FIG. 2A. As further described in connection with FIG. 4 and FIG. 4A, this permits the early VAP model 201c and late VAP model 202c to be activated at different times, e.g., before and after n days of MV or ICU admission time. In one example, "n days" is equal to 4 days, although this parameter may be modified, e.g., via user input or remote model update such as based on a new published guideline accessible on the internet or over a network. As described further herein, the early VAP model 201c and late VAP model 202c may communicate with or modify one another, such as via using a prediction of the early VAP model 201c to influence the late VAP model 202c.

As shown in FIG. 1, predictions from the early VAP model 201c and late VAP model 202c may be provided to different recipients in a variety of forms. In the example of FIG. 1, a communication module 110 communicates the prediction results with different endpoints depending on the use case. The communication module 110 may include a caregiver-facing dashboard that could be integrated into a monitor, such as patient physiological monitor 111 or a monitor associated with the patient bed 101. In an embodiment, the communication module may provide prediction results to remote or mobile devices, e.g., remotely accessible by the caregivers. In the bedside dashboard, which could be a display on the ventilator 102 itself, a real-time overlay of VAP scores on the ventilator panel may be displayed.

Figure 3:
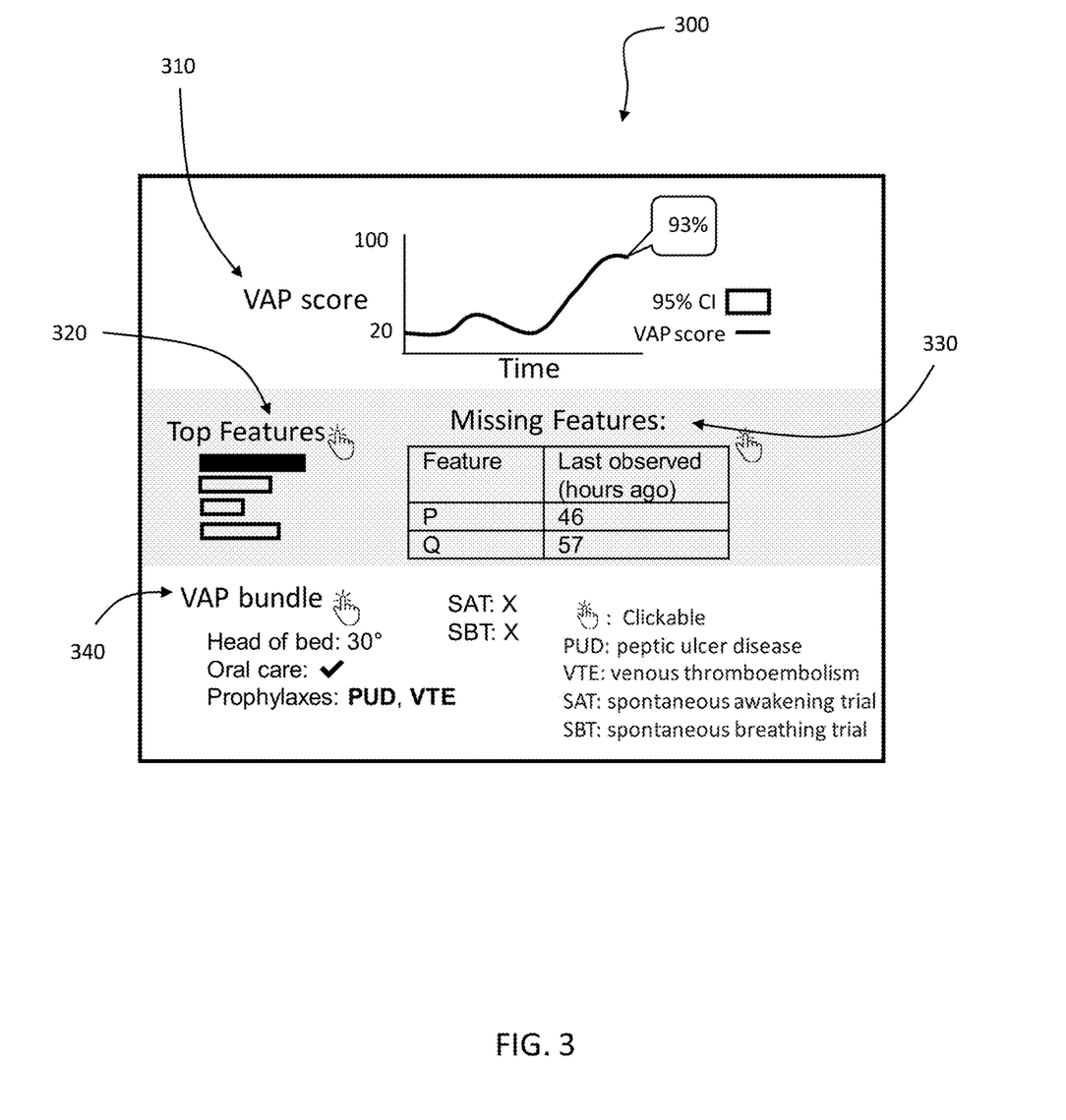
FIG. 3 illustrates an example of indication data produced by a system that automatically predicts VAP.

By way of example, as illustrated in FIG. 3, a monitor or display 300 may be configured to include VAP prediction data. In the example of FIG. 3, a display 300 may include a VAP score area 310, which may present a history or trend of VAP probabilities and confidence intervals as predicted using prediction model(s). In the example of FIG. 3, a VAP is predicted with a current score of 93% and a historical trend line is shown. The display 300 may include additional data areas, such as top features area 320, e.g., regarding features of the patient that are most salient to the VAP prediction score, such as temperature, bicarbonate level, etc., or missing features area 330, e.g., features that are typically of interest but are missing and are not current. Furthermore, in FIG. 3, the display 300 may include a VAP bundle area 340, which may present data relevant to the patient's ongoing care that are associated with or may impact a current or future VAP prediction, such as completion status of oral care for the patient, bed angle, spontaneous awakening or breathing trial completions, other data or recommendations, etc.

Referring again to FIG. 1, in an embodiment the communication module 110 may communicate with or be in the form of a central dashboard (e.g., ICU central station) where the central dashboard displays the most recent VAP risk scores computed for all the mechanically-ventilated patients with an indication, e.g., a flag indicating the patients with a high risk of VAP development and hence in need of intervention. This data allows the caregivers to monitor the patients remotely and attend to those in need of urgent care. In an embodiment, the central dashboard can also display a retrospective, longitudinal view of risk scores for a patient with highlights of relevant features (signs and biomarkers) from different modalities used to compute the scores, similar to the example of FIG. 3.

The VAP prediction data may be provided to and displayed on a patient (physiological) monitor 111. The patient monitor 111 monitors and reports patient vitals routinely and in some cases at a set frequency (e.g., respiratory rate, heart rate). This information is used by a clinician to assess patient status. The patient monitor 111 may be equipped to communicate with the communicative module 110, which provides the VAP prediction data (either in raw or aggregated format) with other long-term data, e.g., obtained from EMR system 108.

A longitudinal database 109 may be included that stores the computed VAP scores over time along with highlights of cues and features most-salient to the computed scores. In an embodiment, a VAP prediction model may retrieve stored scores and adjust a patient's baseline accordingly for a more accurate prediction. The longitudinal database 109 may connect to EMR or EHR system 108 or other patient management databases with bidirectional communication link to send and retrieve data.

Figure 4:
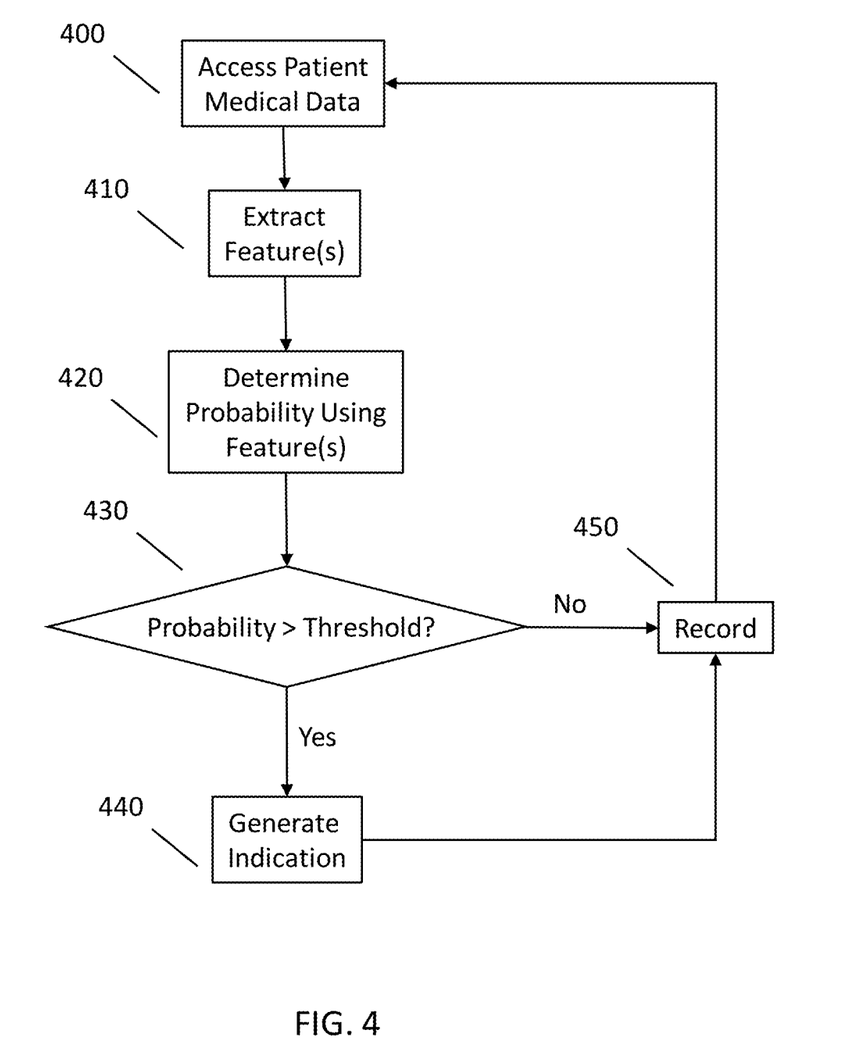
FIG. 4 illustrates an example method for automatically predicting VAP.

Turning to FIG. 4, an embodiment accesses patient medical data at 400, e.g., data derived from a ventilator such as ventilator settings, patient EMR data, etc., to predict a VAP. From this data, features are extracted at 410. In an embodiment, the features extracted at 410 are solely derived from the ventilator, e.g., are ventilator settings such as PEEP and $F_iO_2$. In another embodiment, the data may include other data, such as lab results, patient physiological data (e.g., blood pressure, oral hygiene indication, etc.), diagnosis data, etc., whether derived from a real time monitor or a medical record. In a further embodiment, the data may include data available prior to or at the onset of MV. Accessing of patient medical data at 400 may include accessing data or parameters useful in model selection and activation, as further explained in association with FIG. 4A. By way of example, patient data accessed at 410 may include obtaining an indication of the type of prediction to be performed, e.g., early or late VAP model usage, obtaining data used to influence which segmentation parameter(s) are selected, or obtaining data indicating which feature(s) are to be extracted and provided to the model that is to be activated.

Features of data samples of the patient medical data are extracted at 410 and represented in terms of features that capture descriptive statistics and characterize dynamics of the data streams in each sample (e.g., max, min, median, mean, rate of change). For example, feature types (described below) may be relative over the observation window as compared to a baseline period (e.g., features set to their maximum value minus the mean over a second day of stability (baseline period) to offer patient specific normalization). Feature extraction at 410 may split patient medical data representing ventilator settings and patient physiology into windows, e.g., as illustrated in FIG. 2B. Each window represents a set of data from which a probability of VAP occurrence is predicted. In one example, data is segmented using segmentation parameters to provide an observation window (time in hours from which features for characterizing the patient status are extracted and used for prediction), a window shift (temporal overlap between observation windows, as shown in FIG. 2B), a prediction gap (time in hours in advance of a VAP to be predicted, as shown in FIG. 2B), an event window (temporal offset in hours around a VAP that is predicted, as shown in FIG. 2B), and a marker of the event that is used to position the event within the event window, e.g., $t_v$, as shown in FIG. 2B.

The process of accessing and segmenting the data may be subjected to an optimization process or a user may manually indicate preferred settings, e.g., indicate data streams to be utilized, features of interest, etc. An optimization process may include determining which parameters are suitable for use, evaluated according to a function, for example evaluating parameters against the resultant area under the receiver operating curve (true positive versus false positive) and area under the curve of precision recall (true positive rate vs positive predictive value). By way of specific example, a particle swarm optimization may be used to select a set of observation window, prediction gap and event window parameters. In other embodiments, different optimizers may be used, e.g., a tree-structured Parzen estimator (TPE).

An embodiment may extract one or more of the following features or feature types at 410 to use in predicting the probability of a VAP: vital signs (e.g., respiratory rate, diastolic blood pressure, mean blood pressure, peripheral oxygen saturation, systolic blood pressure, temperature), lab results (e.g., glucose, albumin, pH, hematocrit, oxygen saturation, partial pressure of oxygen, sodium, blood urea nitrogen, white blood cell count, bicarbonate, chloride, hemoglobin, lactate, platelet count, creatinine, potassium, lymphocytes), care status (e.g., head of bed (angle), oral hygiene indication), ventilator-related settings and variables ($F_iO_2$, PEEP, peak inspiratory pressure (PIP), Pplateau (plateau pressure), tidal volume) urine output, admission diagnosis, type of ICU, demographics (e.g., height, weight, gender), sedative drug administration, Glasgow coma scores (e.g., total, eye movement, verbal, motor), and temporal features (e.g., describing temporal progress such as the day and hour of mechanical ventilation). As will be appreciated, the nature and types of features and their extraction and representation may be modified, e.g., based on data availability, data format, the model utilized, the model's development over time, etc.

The extracted features for each sample (observation window) are positive if 1) the observation window overlaps with an event window (FIG. 2B) or 2) their corresponding prediction gap overlap with the event window. The prediction model in one example is a trained model selected from an early VAP model 201c and a late VAP model 202c, e.g., trained on prior data to learn to select and weight the features important for predicting an early-onset VAP and late-onset VAP, respectively. In an embodiment, the trained prediction model may be a gradient boosted trees type classifier, e.g., XGBoost. In other embodiments, the trained prediction model may be another type of classifier, e.g., regularized binomial logistic regression or random forest.

In an embodiment, the model is used at 420 to evaluate features and determine a probability of a VAP. The trained model may be used to classify similar data, i.e., may be provided to a ventilator or associated device and thereafter used to evaluate the patient medical data streamed in at 420 in order to predict VAP. In an embodiment, the model used at 420 may be an ensemble class of models where each model in the ensemble is trained on a different subset of data. These different data subsets can represent different bootstrap samples of the data or data specific to a modality. In either case, the ensemble of models enables estimating uncertainty around the estimated risk for VAP infection as a 95 percentile of the risks estimated by each individual model (expert) in the ensemble.

As shown in FIG. 4, the features are evaluated to determine a probability score for a VAP at 420, e.g., a VAP score as shown in FIG. 3. When a VAP score for a patient meets or passes a set threshold, as determined at 430, an indication may be generated and provided, as indicated at 440. This allows caregivers to be notified to promote timely and personalized treatment regiments such as titration of medications and/or intervention. As described in connection with example of FIG. 3, the reported risk score(s) or associated data may be accompanied with recommendation on interventions. In any event, e.g., even if an indication such as an alarm is not generated, the resultant score(s) or other data associated therewith may be recorded at 450, e.g., to an EMR or database, or provided for display.

Figure 4A:
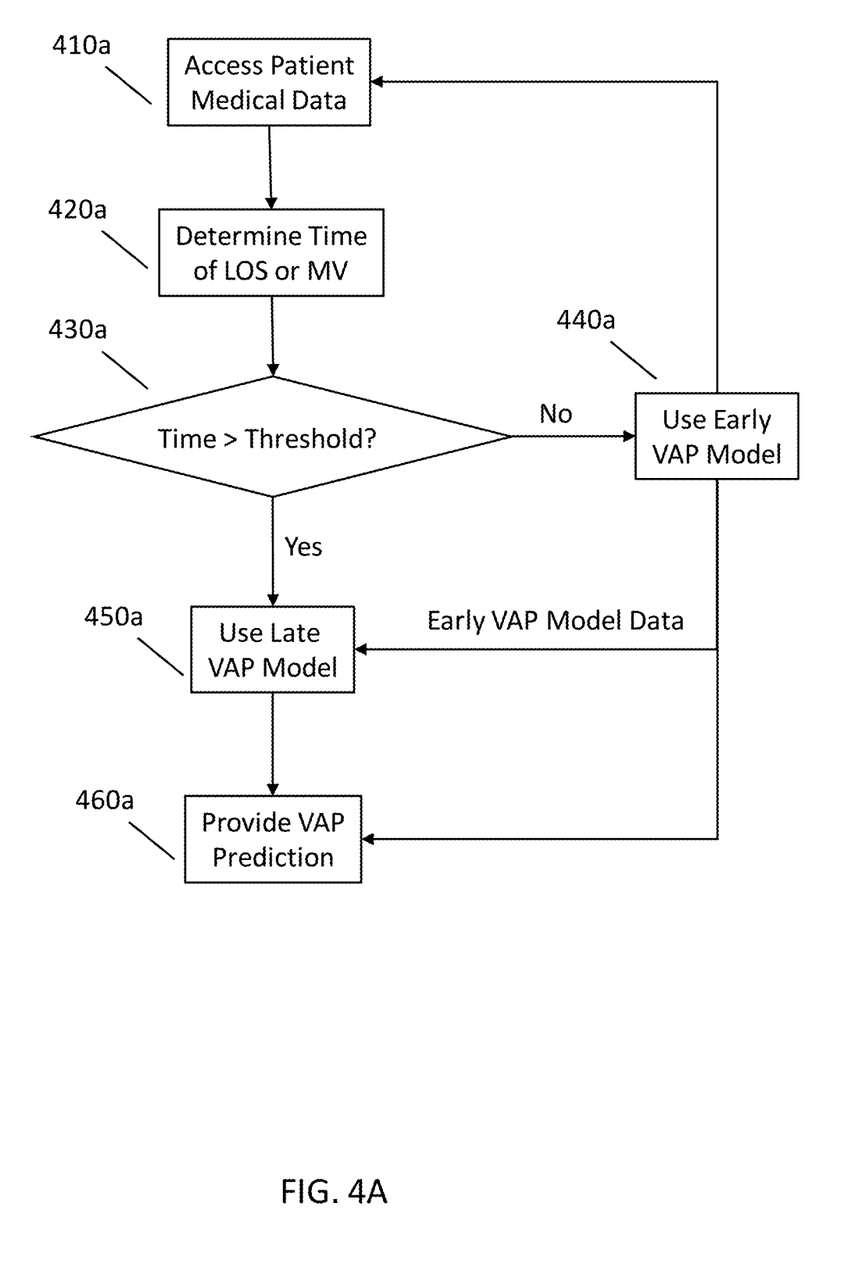
FIG. 4A illustrates an example method of using a hybrid model for automatically predicting VAP.

In an embodiment, as illustrated in FIG. 4A, a hybrid predictive approach is used for predicting early and late VAP events. As illustrated in the example of FIG. 2C, a prediction is mediated explicitly by a timing consideration such as the length of stay (LOS) in the ICU or MV time at the point of prediction. The LOS information may be incorporated into the modeling configuration as in the example of FIG. 4A.

Patient medical data is accessed at 410a, e.g., a patient EMR, a ventilator setting, etc. At 420a a time parameter associated with MV time is determined from the patient medical data, e.g., the LOS or MV time duration. The time parameter is compared to a threshold at 430a. For example, data acquisition module 103 may obtain the LOS time from a ventilator 102 or EMR system 108 and data processing module 105 may compare this time to a threshold, as indicated at 430a. Depending on the comparison of the time parameter with a threshold as indicated at 430a, an embodiment activates a corresponding model at 440a or 450a, based on when a VAP prediction is being made (e.g., before or after a $4^{th}$ day of ICU stay). For example, data processing module 105 may include a subroutine that checks a MV time or time resident in an ICU for the patient, associates this time with a prediction routine, e.g., a schedule of generating one or more predictions using the models, and activates an appropriate model. Each model is capable of providing a VAP prediction as indicated at 460a, with the models being specifically tuned or trained to identify early-onset or late-onset VAP. As indicated in FIG. 4A, at the point or time range of transition to activation of a late VAP model, e.g., a VAP prediction made late in the early VAP period or near the beginning of the late VAP period of FIG. 2C, an embodiment may combine the early VAP model and the late VAP model for combined use. For example, an embodiment uses the most recent early VAP model prediction score as a feature provided as input to the late VAP model. This hybrid modeling also allows for identification of features most salient to each of early and late VAP.

Figure 5:
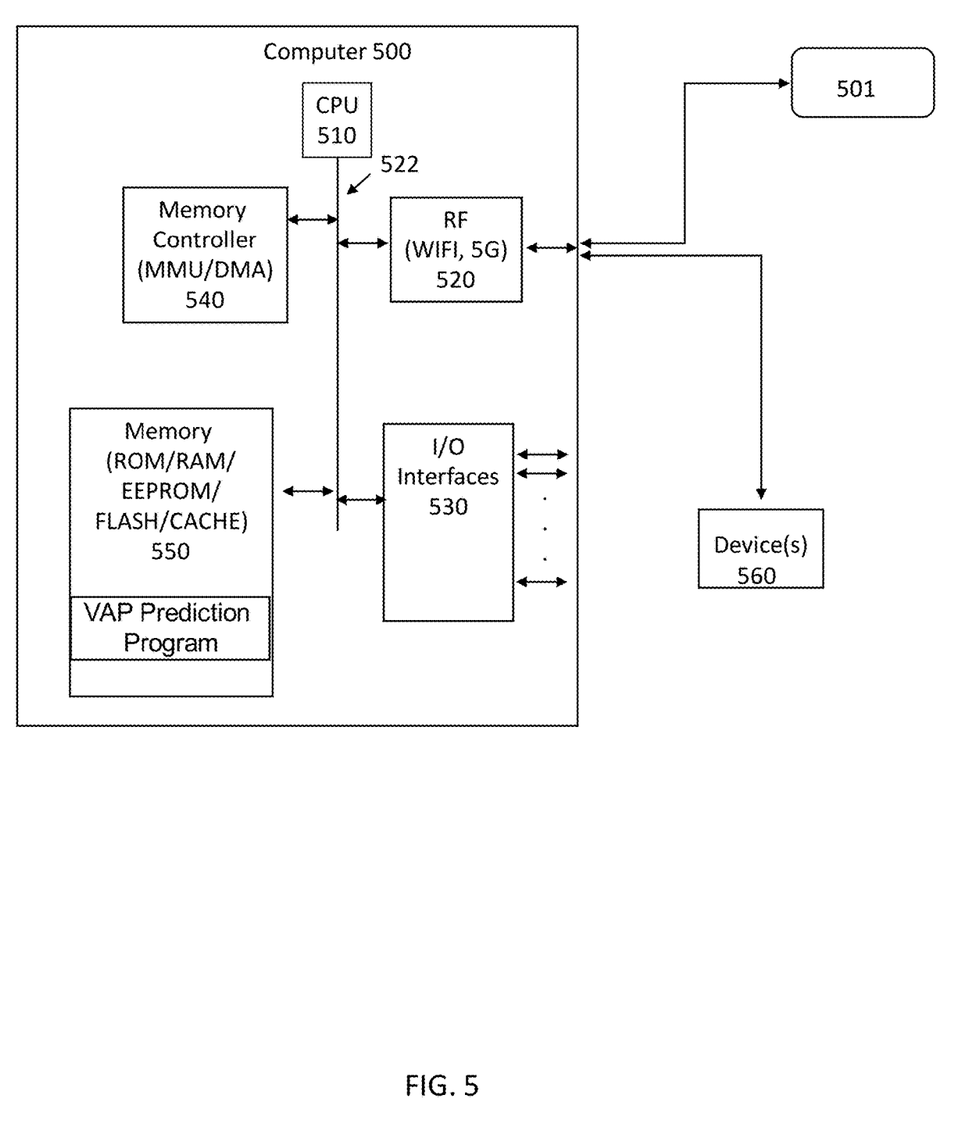
FIG. 5 illustrates an example system in accordance with an embodiment.

Referring to FIG. 5, it will be readily understood that certain embodiments can be implemented using any of a wide variety of devices or combinations of devices. In FIG. 5 an example of system components included in a computer 500 is illustrated, which may be used in implementing one or more embodiments, e.g., as a device used to implement a VAP prediction process as described herein. A system on chip (SoC) or similar circuitry outlined in FIG. 5 may be implemented in a variety of devices, for example similar circuitry may be included in ventilator device 102, as part of a communication module 110, or another device or platform. In addition, circuitry other than a SoC, an example of which is provided in FIG. 5, may be utilized in one or more embodiments. The SoC of FIG. 5 includes functional blocks, as illustrated, integrated onto a single semiconductor chip to meet specific application requirements.

The central processing unit (CPU) 510, which may take the form of or include one or more graphics processing units (GPUs) and/or micro-processing units (MPUs), includes an arithmetic logic unit (ALU) that performs arithmetic and logic operations, instruction decoder that decodes instructions and provides information to a timing and control unit, as well as registers for temporary data storage. The CPU 510 may comprise a single integrated circuit comprising several units, the design and arrangement of which vary according to the architecture chosen.

Computer 500 also includes a memory controller 540, e.g., comprising a direct memory access (DMA) controller to transfer data between memory 550 and hardware peripherals. Memory controller 540 includes a memory management unit (MMU) that functions to handle cache control, memory protection, and virtual memory. Computer 500 may include controllers for communication using various communication protocols (e.g., I²C, USB, etc.).

Memory 550 may include a variety of memory types, volatile and nonvolatile, e.g., read only memory (ROM), random access memory (RAM), electrically erasable programmable read only memory (EEPROM), Flash memory, and cache memory. Memory 550 may include embedded programs and downloaded software, e.g., software such as a VAP prediction program which incorporates or has access to early and late VAP models. By way of example, and not limitation, memory 550 may also include an operating system, application programs, other program modules, and program data, which may be downloaded, updated, or modified via remote devices such as device(s) 560. In one example, an application or program module such as a VAP prediction module may be downloaded or updated over a network or data connection. Such a technique may be used to initiate or install a VAP prediction module, e.g., to update or change an existing VAP prediction module, e.g., for another patient population, updated guidelines, etc.

A system bus 522 permits communication between various components of the computer 500. I/O interfaces 530 and radio frequency (RF) devices 520, e.g., WIFI and telecommunication radios, may be included to permit computer 500 to send and receive data to and from remote devices using wired or wireless mechanisms. The computer 500 may operate in a networked or distributed environment using logical connections to one or more other remote computers or databases. The logical connections may include a network, such local area network (LAN) or a wide area network (WAN), but may also include other networks/buses. For example, computer 500 may communicate data with and between a ventilator 102 and other devices, e.g., a patient monitor 111, a database 109, caregiver devices 501, or other remote device(s) 560, etc.

The computer 500 may therefore execute program instructions configured to store and analyze patient medical data related to ventilated patient conditions within an ICU context in order to predict VAP and perform other functionality of the embodiments, as described herein. A user can interface with (for example, enter commands and information) the computer 500 through input devices, which may be connected to I/O interfaces 530. A display or other type of device may be connected to the computer 500 via an interface selected from I/O interfaces 530.

It should be noted that the various functions or modules described herein may be implemented using instructions or code stored on a memory, e.g., memory 550, that are transmitted to and executed by a processor, e.g., CPU 510. Computer 500 includes one or more storage devices that persistently store programs and other data. A storage device, as used herein, is a non-transitory computer readable storage medium. Some examples of a non-transitory storage device or computer readable storage medium include, but are not limited to, storage integral to computer 500, such as memory 550, a hard disk or a solid-state drive, and removable storage, such as an optical disc or a memory stick.

Program code stored in a memory or storage device may be transmitted using any appropriate transmission medium, including but not limited to wireless, wireline, optical fiber cable, RF, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In an embodiment, program code may be stored in a non-transitory medium and executed by a processor to implement functions or acts specified herein. In some cases, the devices referenced herein may be connected through any type of connection or network, including a local area network (LAN) or a wide area network (WAN), or the connection may be made through other devices (for example, through the Internet using an Internet Service Provider), through wireless connections or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions (computer code) may be provided to a processor of a device to produce a special purpose machine, e.g., a ventilator with VAP prediction capabilities, such that the instructions, which execute via a processor of the device implement the functions/acts specified.

It is worth noting that while specific elements are used in the figures, and a particular ordering of elements has been illustrated, these are non-limiting examples. In certain contexts, two or more elements may be combined, an element may be split into two or more elements, or certain elements may be re-ordered, re-organized, or omitted, as appropriate, as the explicit illustrated examples are used only for descriptive purposes and are not to be construed as limiting.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method of predicting ventilator associated pneumonia (VAP), comprising:
    accessing, using a processor, data of a patient comprising one or more features;
    determining, using a processor, a time parameter associated with mechanical ventilation of the patient;
    using the time parameter to activate one of an early VAP model and a late VAP model to provide an activated model; and
    providing, using a processor, a prediction that VAP will occur based on the activated model operating on the one or more features of the patient data.

2. The method of claim 1, wherein the time parameter indicates a time the patient has been in an intensive care unit.

3. The method of claim 2, wherein the one or more features include one or more of lab results, coma scores, temporal data, and patient physiological data.

4. The method of claim 1, wherein the data of the patient is derived from a ventilator.

5. The method of claim 1, wherein the data of the patient is derived from one or more of a ventilator and an electronic health record.

6. The method of claim 1, wherein the providing comprises utilizing one or more of the early VAP model and the late VAP model as trained using a dataset comprising data associating the one or more features with a mechanical ventilation time.

7. The method of claim 1, wherein the late VAP model is adjusted based on the time parameter.

8. The method of claim 7, wherein the activating comprises:
    using the time parameter to activate the late VAP model; and
    providing data related to an output of the early VAP model to the late VAP model.

9. The method of claim 8, wherein the data related to an output of the early VAP model comprises a most recent prediction of the early VAP model.

10. The method of claim 9, wherein the providing comprises providing data configured to display an indication on a display device associated with one or more of a ventilator, a patient monitor, a central monitor and a remote device.

11. A system for predicting ventilator associated pneumonia (VAP), comprising:
an output device;
a processor operatively coupled to the output device; and
a memory operatively coupled to the processor, the memory comprising processor-executable code comprising:
code that accesses data of a patient comprising one or more features;
code that determines a time parameter associated with mechanical ventilation of the patient;
code that uses the time parameter to activate one of an early VAP model and a late VAP model to provide an activated model; and
code that provides a prediction that VAP will occur based on the activated model operating on the one or more features of the patient data.

12. The system of claim 11, wherein the late VAP model is adjusted based on the time parameter.

13. The system of claim 12, wherein the code that activates comprises:
code that uses the time parameter to activate the late VAP model; and
code that provides data related to an output of the early VAP model to the late VAP model.

14. The system of claim 13, wherein the data related to an output of the early VAP model comprises a most recent prediction of the early VAP model.

15. A ventilator, comprising:
a non-transitory storage medium having processor-executable code comprising:
code that accesses data of a patient comprising one or more features;
code that determines a time parameter associated with mechanical ventilation of the patient;
code that uses the time parameter to activate one of an early VAP model and a late VAP model to provide an activated model; and
code that provides a prediction that VAP will occur based on the activated model operating on the one or more features of the patient data.

16. The ventilator of claim 15, wherein the activated model is the early VAP model;
the ventilator comprising:
code that is configurable to determine a second time parameter;
code that is configurable to determine that the second time parameter exceeds a threshold; and
code that is configurable to transition from use of the early VAP model to the late
VAP model based on the second time parameter;
wherein the late VAP model is thereafter used to provide predictions that VAP will occur based on the one or more features of the patient data.

* * * * *